(12) United States Patent
La Porte et al.

(10) Patent No.: US 8,964,405 B2
(45) Date of Patent: Feb. 24, 2015

(54) PORTABLE ELECTRONIC DEVICE SANITIZER

(75) Inventors: Wesley David La Porte, Morgan Hill, CA (US); Daniel Harrison Barnes, Pittsburgh, PA (US)

(73) Assignee: Phonesoap LLC, Orem, UT (US)

( * ) Notice: Subject to any disclaimer, the term of this patent is extended or adjusted under 35 U.S.C. 154(b) by 111 days.

(21) Appl. No.: 13/615,115

(22) Filed: Sep. 13, 2012

(65) Prior Publication Data

US 2013/0063922 A1 Mar. 14, 2013

Related U.S. Application Data

(60) Provisional application No. 61/533,924, filed on Sep. 13, 2011.

(51) Int. Cl.
*H05K 7/02* (2006.01)

(52) U.S. Cl.
USPC .......................................................... 361/807

(58) Field of Classification Search
USPC .......................................................... 361/807
See application file for complete search history.

(56) References Cited

U.S. PATENT DOCUMENTS

| | | | |
|---|---|---|---|
| 7,424,314 B2 * | 9/2008 | Park ............................... 455/573 |
| 8,203,124 B2 * | 6/2012 | Havens et al. ............ 250/455.11 |
| 8,256,568 B2 * | 9/2012 | Lin ................................. 181/179 |
| 8,522,917 B1 * | 9/2013 | Oh et al. ........................ 181/192 |
| 2002/0009195 A1 * | 1/2002 | Schon ............................ 379/454 |
| 2006/0188389 A1 * | 8/2006 | Levy ................................ 422/24 |
| 2008/0175761 A1 * | 7/2008 | Thur et al. ...................... 422/120 |
| 2010/0044582 A1 * | 2/2010 | Cooper et al. ............ 250/455.11 |
| 2010/0096963 A1 | 4/2010 | McLaughlin et al. |
| 2010/0124040 A1 * | 5/2010 | Diebel et al. .................. 361/816 |
| 2010/0219012 A1 * | 9/2010 | Baumbach ..................... 181/177 |

FOREIGN PATENT DOCUMENTS

| | | |
|---|---|---|
| CN | 101951004 A | 1/2011 |
| KR | 2003033475 A | 5/2003 |
| KR | 2006012144 A | 2/2006 |
| KR | 675770 B1 | 1/2007 |
| KR | 956373 B1 | 5/2010 |
| KR | 2011024651 A | 3/2011 |
| WO | 2006022466 | 3/2006 |
| WO | 2006075894 | 7/2006 |

* cited by examiner

*Primary Examiner* — Forrest M Phillips
(74) *Attorney, Agent, or Firm* — Stoel Rives LLP

(57) ABSTRACT

A personal electronic device (PED) sanitization device comprises a compartment configured to receive a PED and a sanitization module configured to emit electro-optical (EO) radiation into the interior of the compartment. The compartment may comprise a support member configured to maintain the PED at a particular position and/or orientation. The support member may be transparent to the EO radiation, such that the entire surface of the PED can be irradiated. The device may further comprise an acoustic conduit to allow sounds generated by the PED to be transmitted outside of the compartment. The conduit may be configured to prevent EO radiation from leaking into the environment.

20 Claims, 11 Drawing Sheets

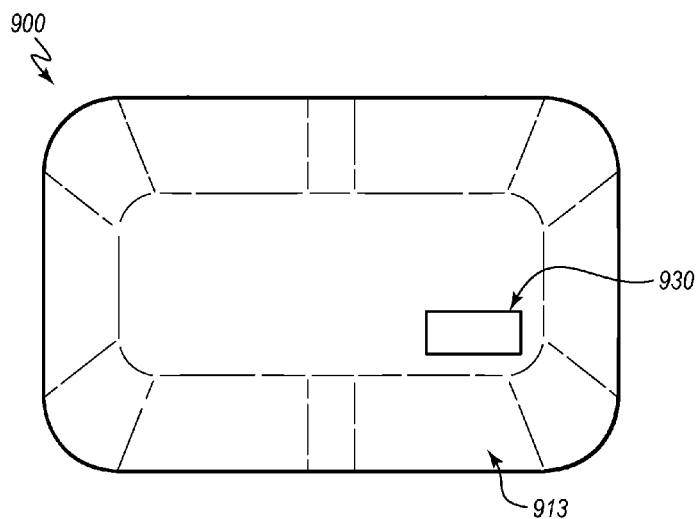
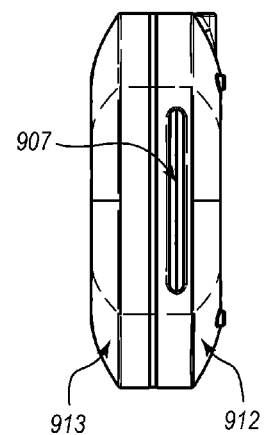
FIG. 9A
FIG. 9D
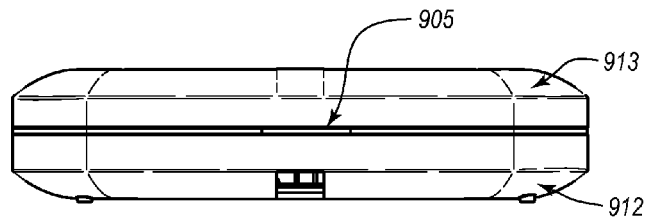
FIG. 9B
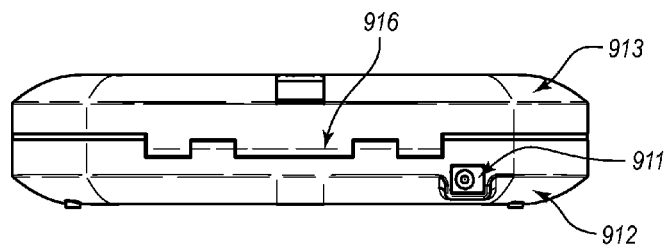
FIG. 9C

PORTABLE ELECTRONIC DEVICE SANITIZER

CROSS-REFERENCE TO RELATED APPLICATIONS

This application claims priority to U.S. Provisional Application No. 61/533,924, entitled "Portable Electronic Device Anti-Microbial Charger," filed on Sep. 13, 2011, and which is hereby incorporated by reference.

TECHNICAL FIELD

The disclosure relates to sanitizing an electronic device, and more specifically, to charging and sanitizing portable electronic devices using electro-optical radiation.

BRIEF DESCRIPTION OF THE DRAWINGS

This disclosure includes and references the accompanying drawings, which provide a more particular description of the embodiments disclosed herein. The disclosure, however, is not limited to the particular embodiments depicted in the figures. The teachings of the disclosure may be utilized and/or adapted to other embodiments, and/or changes may be made to the disclosed embodiments, without departing from the scope of the disclosure.

FIGS. 9A-D depict embodiments of an apparatus for sanitizing a portable electronic device in a closed configuration;

DETAILED DESCRIPTION

Figure 1:
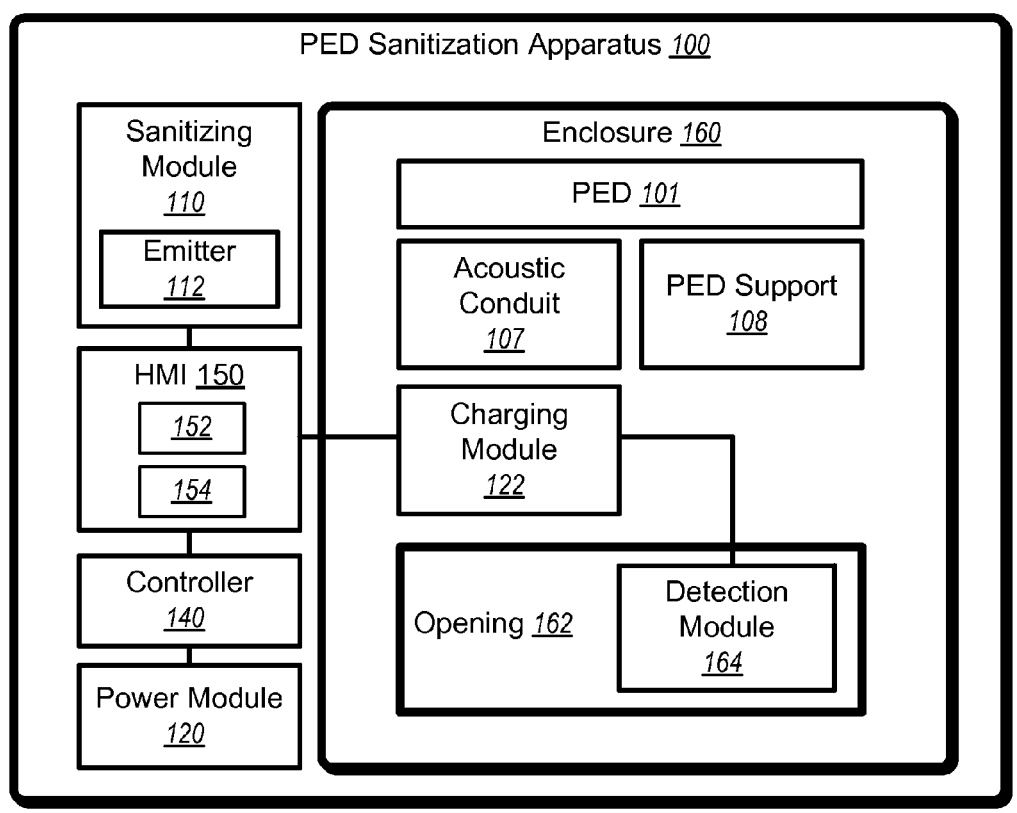
FIG. 1 is a block diagram of one embodiment of a portable device sanitizer.

The surfaces of portable electronic devices tend to attract and harbor potentially harmful organisms, such as microbes, pathogens, viruses, bacteria and the like. Disclosed herein are embodiments of apparatus, systems, and methods for sanitizing a portable electronic device (PED). The disclosed embodiments may provide for charging the PED while the PED is being sanitized. In some embodiments, the PED is sanitized by use of electro-optical (EO) radiation. Certain wavelengths of Ultraviolet (UV) radiation may be used to sanitize a PED. As used herein, EO radiation or "sanitizing EO radiation" refers to any suitable wavelength and/or type of EO radiation capable of sanitizing a surface, such radiation may include, but is not limited to: type-C ultraviolet radiation (UV-C) comprising wavelengths between 280-100 nm, type B ultraviolet radiation (e.g. UV-B), middle ultraviolet radiation (MUV), far ultraviolet radiation (FUV), ionizing EO radiation, non-ionizing EO radiation, a combination of wavelengths and/or EO radiation types, or the like.

The PED sanitizer disclosed herein may be configured to irradiate a PED for different amounts of time. Some types of EO radiation may be capable of sanitizing the surface of a PED relatively quickly (e.g., 3-5 minutes of exposure to UV-C may be sufficient to sanitize a surface). In some embodiments, the EO radiation exposure time may adapted in accordance with the intensity of the emitted EO radiation, type(s) of EO radiation used to irradiate the PED, user configuration and/or preferences, or the like. In some embodiments, the amount of EO exposure is configurable by a user (e.g., via button, selector, timer, or other human-machine-interface component). Alternatively, or in addition, the amount of exposure may be automatically determined based upon properties of the EO radiation, time since a last sanitization cycle for the PED, and/or other suitable factors.

In some embodiments, the PED sanitizer may be configured to sanitize a PED using a single wavelength of sanitizing EO radiation. In other embodiments, multiple wavelengths of EO radiation may be used, comprising a composite emission of sanitizing EO radiation. In some embodiments a series of different wavelengths of sanitizing EO radiation may be applied according to a particular sequence or pattern. Where multiple wavelengths of sanitizing EO radiation are used, the particular wavelengths applied to the PED may be configured to target a specific organism (e.g., a specific type of bacteria). The particular wavelength may also be selected to avoid damage to the PED (e.g., may be selected to avoid damaging the finish, materials, case, and/or operational components of the OED). For example, the EO radiation wavelengths may be selected, such that the EO radiation will sanitize the surface of the OED, while minimizing harm to the plastics, composites, metals, alloys, fabrics, pigments or dyes used in the construction of the PED. In some embodiments, wavelengths may be selected to minimize penetration of the EO radiation into the interior of the PED and/or wavelengths that will not adversely affect the electronics, processor, memory, storage, and/or other components of the PED.

The PED sanitizer disclosed herein may be configured to sanitize any number of different types of devices, including, but not limited to: portable telephone, a cordless telephone, a smart phone, a wireless headset, a portable media device, a digital camera, a video recorder, an audio recorder, a portable gaming device, a portable computing device, a tablet computer, laptop computer, notebook computer, an electronic reading device, a personal digital assistant (PDA), a palmtop computer, a handheld computer, a pen computer, a ultra-mobile personal computer, a pager, a portable navigation device, a personal navigation assistant (e.g., portable Global Positioning System (GPS) unit), or the like.

As disclosed herein, an apparatus for sanitizing a PED may comprise an interior enclosure or compartment configured to receive a PED and a sanitizing module comprising one or more EO emitters. The apparatus may further comprise a support member configured to maintain the PED at a particular orientation and/or position within the enclosure. In some embodiments, the support member may be transparent (or substantially transparent) to the EO radiation emitted by the EO emitters and/or the interior surface of the enclosure may be configured to reflect EO radiation, such that the EO emitter is capable of irradiating the entire surface of the PED. The apparatus may further comprise a charging module configured to charge the PED while the PED is within the enclosure or compartment (and/or while the PED is being sanitized by the EO radiation). In some embodiments, the apparatus may comprise one or more indicators configured to display sanitization and/or charging status information to a user.

The apparatus may be configured to limit activation of the sanitization module (and/or EO emitters). In some embodiments, the EO emitters may be configured to emit EO radiation in response to determining that the enclosure is in a closed configuration (e.g. is sealed). As used herein, a "closed" or "sealed" configuration refers to a configuration in which the interior region, portion, and/or compartment of the apparatus is closed with respect to the transmission of EO radiation, such that there is no optical transmission path from the interior of the apparatus to the exterior of the apparatus and/or EO radiation of the emitter is not radiated to the exterior of the apparatus (e.g., the EO radiation does not escape the interior compartment). By contrast, in an "open" configuration, the interior of the apparatus is accessible, such that EO radiation emitted therein would be capable of radiating from the apparatus. In the open configuration, the PED may be placed within the apparatus and/or removed from the apparatus.

In some embodiments, the PED sanitization apparatus may comprise a detector module configured to determine whether the apparatus is closed. The PED sanitization apparatus may be configured to activate the sanitization module (e.g. EO emitter) in response to determining that the apparatus is in a closed or sealed configuration. The sanitization module may be deactivated in response to the detector module determining that the apparatus is in an open or unsealed configuration. The detector module may comprise one or more detection mechanisms including, but not limited to: contact switches, conductive switches, magnetic switches, capacitive switches, resistive switches, latches, or the like. In some embodiments, the detector module may comprise a plurality of redundant detection mechanisms, and the sanitization module may be activated in response to each of the detection mechanisms indicating that the apparatus is in a closed or sealed configuration.

In some embodiments, the PED sanitization apparatus may comprise an enclosure comprising of an upper portion and a lower portion. The upper and lower portions may form a clamshell, and may define an interior portion configured to receive the PED. In some embodiments, an apparatus for sanitizing a portable device comprises an enclosure and a lid wherein the lid may be opened so that a PED can be placed into the enclosure. In yet another embodiment the apparatus comprises an enclosure and a drawer wherein the drawer is configured to slide or rotate out of the enclosure so that a PED can be placed therein. The drawer may comprise a tray or other support member configured receive a PED. In some embodiments, the tray comprises a rim, lip, or raised portion extending from the tray to prevent the PED from sliding off the tray when the drawer is opened and/or closed.

FIG. 1 is a block diagram of one embodiment of a PED sanitization apparatus 100. The PED sanitization apparatus 100 may comprise a sanitizing module 110, a power module 120, a charging module 122, a detection module 164, and a controller 140. The controller 140 may be communicatively coupled to the sanitizing module 110, power module 120, and the charging module 122. The controller 140 may be configured to control the operation of the sanitizing module 110 and/or charging module 122, which may comprise selectively activating and/or deactivating the sanitizing module 110 and/or charging module 122.

The apparatus 100 may further comprise a human-machine interface (HMI) module 150. The HMI module 150 may comprise one or more input/output components, such as buttons, switches, displays, and the like. The HMI module 150 may comprise a status indicator module 152 configured to display and/or communicate status information pertaining to the PED sanitization apparatus 100, such as current sanitization status, sanitization time, charge status, charge time, powered-on state, closure state of the enclosure 160, and so on. In some embodiments, the status indicator module 152 comprises one or more visual indicators, such as a Liquid Crystal Display (LCD), one or more light emitters, or the like. The status indicator module 152 may comprise one or more acoustic indicators designed to produce sounds or speech to indicate the sanitizing and/or charging status. The acoustic indicator may be a speaker, a vibrator, or any other mechanism configured to generate vibrations or other acoustic signals. The HMI module 150 may further comprise an input module 154 configured to receive user input and/or configuration information, such as sanitization time and/or mode parameters, charge settings, and so on.

The PED sanitization apparatus 100 may further comprise an enclosure 160 configured to receive a PED 101 via an opening 162. The opening 162 may comprise a clamshell configuration (e.g., an upper member and a lower member), a tray, or the like. The enclosure 160 may comprise a closed configuration and an open configuration. As described above, in the closed configuration, the enclosure 160 may be sealed with respect to EO radiation, such that EO radiation emitted therein (e.g., by the emitter 112 of the sanitizing module 110) is not emitted outside of the enclosure 160. The enclosure 160 may comprise a detection module 164 configured to detect whether the enclosure 160 is in the closed configuration. The detection module 164 may be configured to communicate the closure status of the enclosure 160 to the controller 140. The controller 140 may be configured to deactivate the sanitizing module 110 when the enclosure 160 is not in the closed configuration. As described above, the detection module 164 may comprise one or more detection mechanisms, such as switches, latches, or the like.

The sanitizing module 110 may be configured to emit EO radiation into an interior of the enclosure 160. The EO radiation may be configured to irradiate the surface of the PED 101 within the enclosure 160. The sanitizing module 110 may be configured to emit EO radiation at one or more wavelengths, which, as described above, may be configured to kill, and/or render harmless, organisms on the surface of the PED 101 (e.g., bacteria). In some embodiments, the sanitizing module 110 is configured to emit a single wavelength of EO radiation. In other embodiments, the sanitizing module 110 is configured to emit a broad spectrum of sanitizing EO radiation. The sanitizing module 110 may be configured to emit multiple discrete wavelengths or multiple narrow spectrums of EO radiation. In some embodiments, the sanitizing module 110 is configured to emit EO radiation at wavelengths between 240 nm and 280 nm, which may disrupt the chemical bonds of DNA and RNA, thereby killing microorganisms. Radiation emitted at these wavelengths is also known to break down organic molecules and carbon-based molecule. In some embodiments, a wavelength of the EO radiation is selected to be suitable for breaking down particles of grease or skin oil. In some embodiments, the emitted wavelengths of EO radiation are preselected. In other embodiments the emitted wavelengths are selected by the user, for example by the user selecting a set of wavelengths or indicating a choice between a plurality of preset combinations of wavelengths via the HMI 150.

The sanitizing module 110 may comprise an emitter 112 configured to emit EO radiation of an appropriate wavelength and/or intensity to sanitize the PED 101, as described above. The emitter 112 may be located in a suitable position within the enclosure 160 so that the entire surface of the PED 101 is exposed to the EO radiation. In some embodiments, the sanitizing module 110 may comprise a plurality of emitters 112 configured to irradiate the PED 101 from different locations, angles, and/or positions within the enclosure 160.

In some embodiments, a single emitter 112 is used, and EO radiation emitted therefrom is reflective, refracted, and/or diffused within the enclosure 160 (by an inner surface of the enclosure 160). In some embodiments, one or more emitters 112 are located directly above or below the PED device and EO radiation is propagated through the interior portion by means of reflective and/or refractive surfaces. In other embodiments, one or more emitters 112 are disposed at the side of the PED device 101 and EO radiation is propagated through the enclosure 160 by means of reflective and/or refractive surfaces. In yet other embodiments, a plurality of emitters are located throughout the enclosure 160.

The emitter 112 may comprise any suitable EO radiation source, including, but not limited to, a light emitting diode (LED), a laser, an electric arc discharge, a gas-discharge lamp, a fluorescent lamp, or the like. In some embodiments, the emitter 112 is configured to be compact to minimize the size requirements of the apparatus 100. In another embodiment, a larger dimensioned emitter(s) 112 may be used.

The emitter 112 may further comprise one or more lenses for distributing, focusing, spreading, or otherwise directing EO radiation emitted thereby to particular portions of the interior of the enclosure 160. The emitter 112 may further comprise one or more filters capable of blocking unwanted portions and/or wavelengths of EO radiation. As a non-limiting example, a low-pressure mercury-vapor lamp emits EO radiation at peak wavelengths of approximately 184 nm and 254 nm. While both wavelengths can be used to sanitize a PED, EO radiation of 184 nm will also produce ozone, which may be undesirable. Accordingly, the low-pressure mercury-vapor lamp may be used in conjunction with a filter designed to block 184 nm EO radiation while passing through 254 nm EO radiation.

As disclosed above, the enclosure 160 may comprise an interior portion or region configured to receive the PED 101. An inner surface of the enclosure 160 may be configured to direct EO radiation to the PED 101. Accordingly, in some embodiments, portions of the interior surface of the enclosure 160 may comprise reflective material configured to reflect emitted EO radiation to the PED 101 such that the entire surface of the PED 101 is exposed thereto. In some embodiments, substantially all of the surface of the enclosure 160 is configured to reflect EO radiation. Alternatively, only certain portions of the surface may be comprised of reflective material (e.g., portions that face the PED 101). In embodiments where reflective material is used, the PED 101 may be exposed to reflected sanitizing EO radiation that reaches the PED 101 at oblique angles to minimize shadowing on the surface of the PED 101. The shadowing may be caused, for example, by particles on the surface of the PED 101, by features, such as seams or buttons, on the surface of the PED 101, or by scratches or other flaws in the surface of the PED 101. In yet another embodiment, no reflective material is used, but rather the emitters 112 of the sanitizing module 110 are arranged so that the entire surface of the PED 110 is directly exposed to EO radiation.

In some embodiments, PED sanitization apparatus 100 may comprise a PED support 108 that is configured to maintain the PED 101 at a particular orientation and/or position within the enclosure 160. The PED support 108 may be configured to maintain the PED 101 in an orientation and/or position configured to allow EO radiation emitted by the emitter 112 irradiate substantially the entire surface of the PED 101. In some embodiments, the PED support 108 may be transparent (or substantially transparent) to the EO radiation emitted by the emitter 112. Accordingly, the PED support 108 may be comprised of EO transparent materials. The support member may be made of glass, plastic, polymer, ceramic, or other suitable materials sufficiently transparent to the EO radiation emitted by the sanitizing module 110. In some embodiments, the emitter 112 may be placed below the PED support 108 such that sanitizing EO radiation is emitted through the PED support 108 onto the surface of the PED 101. The intensity of the emitters 112 located below the PED support 108 may be increased relative to other emitters 112 to compensate for partial absorption of the sanitizing EO radiation by the PED support 108. In some embodiment, the PED support 108 may be configured to filter EO radiation and/or otherwise modify EO radiation emitted by the EO emitter 112.

In some embodiments, the PED support 108 may comprise a flat support member (e.g., plate) configured to hold the PED 101 in a horizontal orientation. In some embodiments, a connector of the charging module 122 may be rigidly attached to the PED 101 such that the PED 101 is secured within the enclosure 160. Alternatively, or in addition, the PED support 108 may comprise a textured surface capable of preventing, or minimizing, movement of the PED 101. In some embodiments, the PED support 108 further comprises raised members that prevent the PED from sliding off of the PED support 108. The raised members may be transparent to the sanitizing EO radiation. In another embodiment, the raised members are reflective to the sanitizing EO radiation.

In some embodiments, the enclosure 160 may comprise an acoustic conduit, opening, or exit 107 configured to provide an acoustic path or channel between an interior of the enclosure 160 and the exterior of the enclosure 160. Sound emitted by the PED 101 within the enclosure 160 may pass through the acoustic conduit 107 to the exterior of the enclosure 160. The acoustic conduit 107 may, therefore, allow to user to hear alerts or alarms generated by the PED 101 while the PED 101 is within the enclosure 160. The acoustic conduit 107 may be further configured to prevent EO radiation from escaping the enclosure 160. Accordingly, the acoustic conduit 107 may be configured to block and/or prevent optical paths between the enclosure 160 and the exterior of the enclosure. In some embodiments, a shape of the acoustic conduit 107 may be configured to block EO radiation; the acoustic conduit 107 may be curved, tapered, and/or otherwise adapted to prevent EO radiation leakage. Alternatively, or in addition, an outer surface of the acoustic conduit 107 may be comprised of materials configured to absorb EO radiation emitted by the emitter 112. The acoustic conduit 107 may be configured such that there is no line-of-sight or optical path from the interior of the enclosure 160 to the exterior of the enclosure 160. In some embodiments, the acoustic conduit 107 comprises a narrow slot leading from the interior of the enclosure 160 to the exterior. In some embodiments the acoustic conduit 107 comprises a membrane of EO radiation absorptive material configured to block EO radiation, while readily passing acoustic signals. In some embodiments filaments of EO radiation absorptive material are placed within the acoustic conduit 107 to absorb sanitizing EO radiation while allowing acoustic signals to pass.

In some embodiments, the enclosure 160 and/or acoustic conduit 107 are configured to amplify sounds therein (e.g., amplify acoustic signals generated within the enclosure 160). In some embodiments the acoustic conduit 107 comprises an acoustic megaphone configured to amplify sound or other acoustic signals originating within the enclosure 160. In some embodiments, the acoustic conduit 107 comprises a horn configured to resonate acoustic signals.

The charging module 122 may be configured to charge or recharge the PED 101. The charging module 122 may comprise a connector configured to supply electrical power to the PED 101. The connector may be a physical connector that plugs into the PED 101, such as a Universal Serial Bus (USB) connector, mini-USB connector, micro-USB connector, 30-pin connector, a proprietary connector, or the like. Alternatively, or in addition, the charging module 122 may comprise an inductive coil to transfer power wirelessly to the PED 101. In some embodiments the connector of the charging module 122 may be further configured to act as a docking connector for the PED 101 (e.g., communicate data between the PED 101 and a computing device, hub, or the like). The PED sanitizing apparatus 100 may be configured to act as an end node of the data connection or may be configured act as an intermediary node (hub) used to establish a data connection between the PED and another, external computing device. In some embodiments the charging module 122 may comprise a removable adaptor capable of connecting to various different types of connectors and/or PEDs. In some embodiments the connector of the charging module 122 is extendable so that the PED 101 can be positioned at different locations and/or orientations within the enclosure 160.

In some embodiments the charging module 122 may comprise a pass-through port configured to allow a cord or cable of a third-party charger to pass into the enclosure 160. The port and/or opening may be configured to prevent EO radiation from escaping the enclosure 160. Accordingly, the port and/or opening may comprise a gasket, pass-through cable, or other mechanisms and/or structures for blocking EO radiation. Alternatively, the charging module 122 may comprise an intermediary cable or cord with an exterior connector for connecting to a third-party charger and an interior connector.

As disclosed above, the controller module 140 may be configured to control the charging and/or sanitizing operations of the apparatus 100. The controller 140 may comprise a microprocessor, an application-specific integrated circuit (ASIC), an integrated circuit, programmable logical array (PLA), or the like. In some embodiments the controller 140 comprises a timer module and/or process configured to track time information pertaining to the operation of the sanitizing module. The controller 140 references the timing information to determine when to cause the sanitizing module 110 to stop emitting EO radiation. The controller 140 may, therefore, control the exposure time of the PED 101. In some embodiments, the controller 140 automatically deactivates the sanitizing module 110 after a predetermined irradiation time. In some embodiments, the exposure time may be determined from user input (received via the HMI 150). In another embodiment, the exposure time is automatically calculated by the controller 140; the exposure time may be selected according the intensity, wavelength, and/or type of EO radiation emitted by the sanitizing module 110. In some embodiments, the amount of exposure time may vary according to the contamination level of the PED 101.

As disclosed above, the controller 140 may be coupled to the detection module 164 to determine whether the enclosure 160 is in a closed configuration. The controller 140 may be configured to deactivate the sanitizing module 110 while the enclosure 160 is not in the closed configuration. The controller 140 may be further configured to monitor the closure status of the enclosure 160 during operation of the sanitizing module 110 (by use of the detection module 164), and may interrupt sanitizing operations in response to determining that the enclosure 160 is no longer in the closed configuration. In some embodiments, the controller 140 may be configured to continue a sanitizing cycle (e.g., re-activate the sanitizing module 110, but not reset a timer associated with the cycle) in response to closing the enclosure 160. In some embodiments, the sanitizing cycle may be configured to continue the sanitizing cycle if the enclosure 160 is closed within a time threshold; otherwise, the controller 140 may be configured to restart the sanitizing cycle.

In some embodiments the controller 140 is configured to automatically activate the sanitizing module 110 in response to detecting a PED 101 within the enclosure 160. In some embodiments the controller 140 determines that a PED 101 is present within the enclosure 160 by determining whether a PED 101 is connected to the charging module 122. In some embodiments, the apparatus 100 comprises one or more sensors configured to determine whether a PED 101 is present within the enclosure 160. Such sensors may include, but are not limited to, optical sensors, weight sensors, capacitive sensors, resistive sensors, pressure sensors, mechanical switches, or the like.

The controller 140 may be configured to periodically perform self-sanitization operations. Accordingly, in some embodiments, the controller 140 may be configured to automatically activate the sanitizing module 110 when the enclosure 160 is closed, regardless of whether the PED 101 is present within the enclosure 160. The self-sanitization cycle may ensure that the enclosure 160 is free of bacteria and/or other contaminants in areas obscured by the PED 101. In some embodiments, a self-sanitization processes may be invoked manually through the HMI 150.

The apparatus 100 may further comprise one or more latching and/or securing mechanisms configured to maintain the enclosure 160 in a closed configuration. The mechanisms may be further configured to prevent EO radiation from escaping the enclosure 160. In some embodiments, the enclosure 160 may comprise a pair of magnets configured to secure two halves of the enclosure 160 to one another. In some embodiments, the enclosure 160 may comprise a spring in a hinge that applies a closing force to thereto. In some embodiments, the enclosure 160 comprises a bi-stable spring, or other suitable mechanism, where one stable state corresponds to a closed configuration and the other stable state corresponds to an open position. In some embodiments the latching mechanism is integrated with the detection module 164 for determining whether the enclosure 160 is in a closed configuration.

In some embodiments, the enclosure 160 may comprise an EO radiation seal configured to prevent leakage of EO radiation. The radiation seal may comprise a gasket, and/or lips formed at the opening 162 of the enclosure 160. In some embodiments, the EO radiation seal(s) may comprise material configured to absorb EO radiation. Portions of the EO radiation seal(s) may be formed from reflective materials configured to reflect EO radiation back into the enclosure 160.

Figure 2:
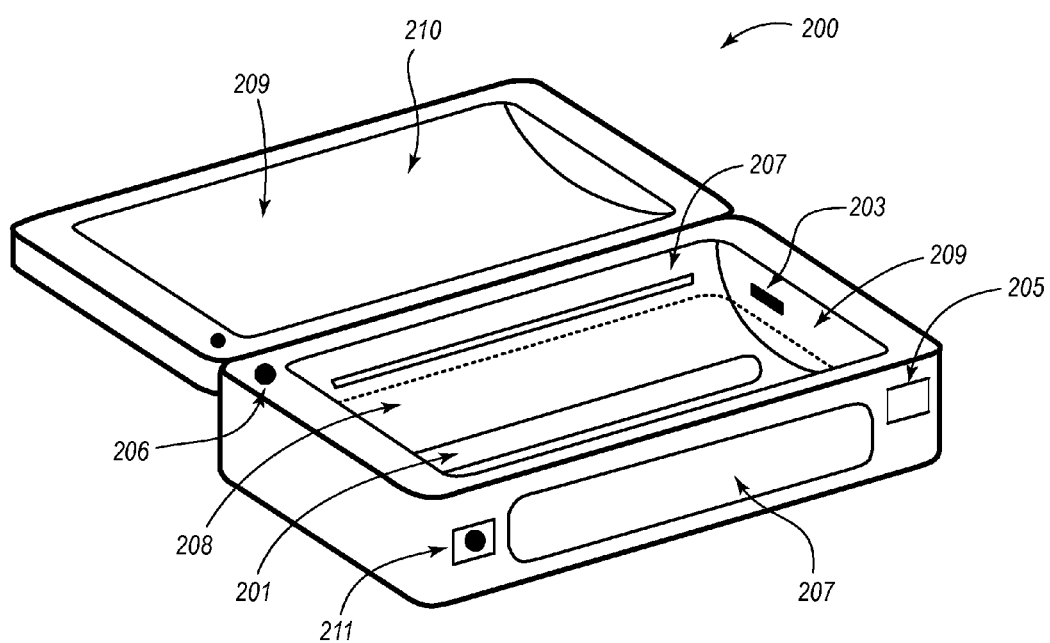
FIG. 2 depicts another embodiment of an apparatus for sanitizing a portable electronic device.

FIG. 2 depicts another embodiment of an apparatus 200 configured to sanitize a PED. The apparatus 200 may comprise a sanitizing module (emitter) 201, charging module 203, status indicator module 205, detection module 206, acoustic conduit 207, PED support 208. The apparatus 200 may comprise a case or enclosure comprising an interior 209 configured to receive a PED. In some embodiments, the apparatus 200 may comprise a case, and the interior 209 may comprise an interior enclosure, portion, or region of the case. The apparatus 200 may further comprise a controller (not shown) configured to control the operation of the emitter 201 and/or charging module 203, as described herein.

The emitter 201 may be configured to emit EO radiation into the interior 209 of the apparatus 200. In the FIG. 2 embodiment, an inner surface 210 of the apparatus 200 may be configured to reflect and/or diffuse EO radiation within interior chamber 209 so that an entire surface of the PED within the apparatus 200 may be exposed to the EO radiation. As shown in FIG. 2, the emitter 201 may be disposed within a lower portion of the apparatus 200. EO radiation emitted from the emitter 201 may be reflected and/or diffused by the inner surface 210, such that an upper portion of a PED within the apparatus 200 is exposed to the EO radiation.

The apparatus 200 may further comprise a PED support 208 configured to maintain a PED within the interior 209 between the emitter and the inner surface 210 (e.g., between a lower and upper region of the apparatus. The support 208 may be transparent to EO radiation; the support 208 may comprise a glass or plastic surface configured to transmit EO radiation emitted by the emitter 201.

In some embodiments, the apparatus 200 may comprise an acoustic conduit 207 configured to provide an acoustic pathway or channel from the interior 209 of the apparatus 200 to the exterior of the apparatus 200. The acoustic conduit 207 may be further configured to block EO radiation from escaping the apparatus 200 (when in the closed configuration). Accordingly, the acoustic conduit 207 may be configured to preclude and/or block optical paths from the interior 209 to the exterior of the apparatus 200. In the embodiment of FIG. 2, the acoustic conduit 207 may be curved, to prevent EO radiation transmission. Alternatively, or in addition, the acoustic conduit 207 may comprise a surface that is configured to absorb EO radiation emitted by emitter 201.

Figure 3:
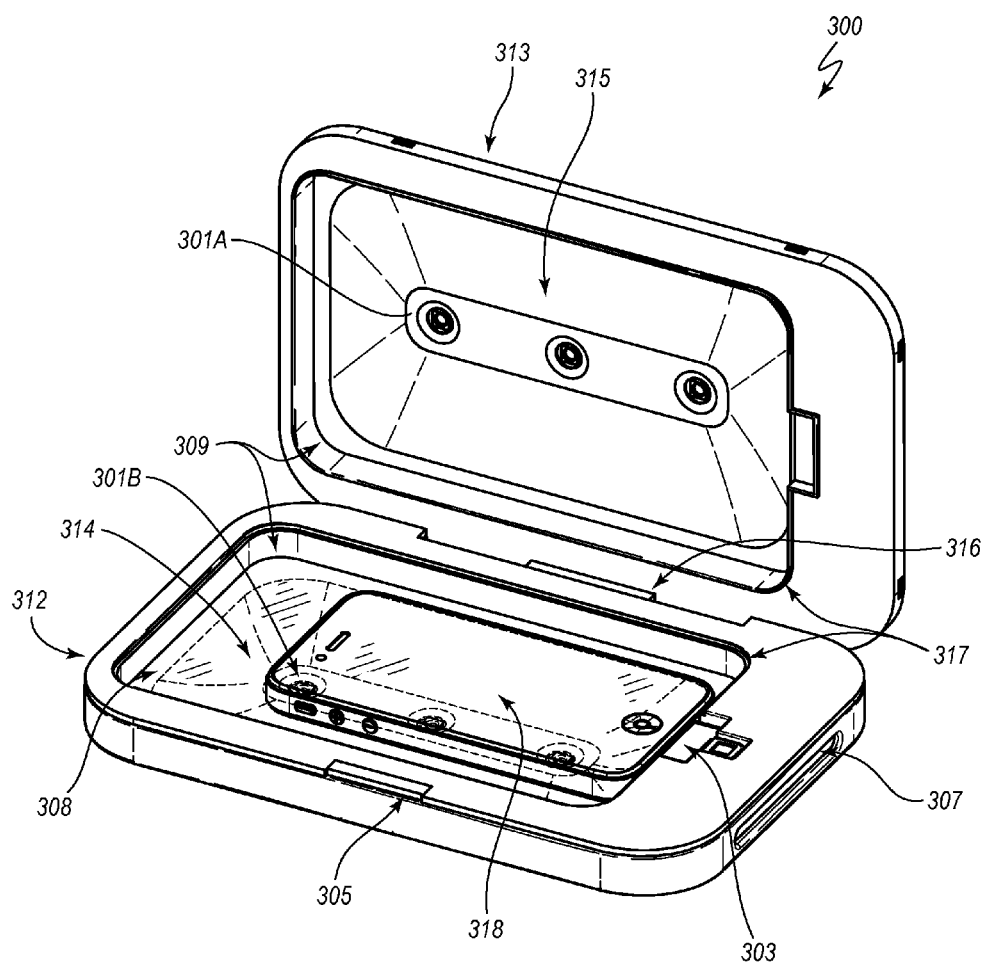
FIG. 3 depicts another embodiment of an apparatus for sanitizing a portable electronic device.

FIG. 3 depicts another embodiment of an apparatus 300 configured to sanitize a PED. In the FIG. 3 embodiment, the apparatus 300 may comprise one or more emitters 301A configured to emit EO radiation from an upper region 313 of the apparatus 300, and one or more emitters 301B configured to emit EO radiation from a lower region 312 of the apparatus 300.

The emitters 301A and 301B may be configured to emit EO radiation, such that an entire surface of the PED 318 is exposed to the EO radiation (e.g., the EO radiation emitted by the emitters 301A and/or 301B reaches substantially all of the surface area of the PED 318). Accordingly, and as depicted in FIG. 3, the PED 318 may be irradiated from the upper portion 313 and the lower portion 312 of the apparatus 300.

The PED 318 may be maintained between the upper 313 and lower 312 regions by a support member 308. The support member 308 may be transparent to EO radiation, such that EO radiation emitted by the emitter 301B irradiates a lower portion of the PED 318 (through the support member 308). In some embodiments, the inner surface 315 of the upper region 313 is configured to reflect EO radiation. Accordingly, EO radiation emitted from the emitters 301B may pass through the support member 308, reflect off of the inner surface 315, and irradiate an upper portion of the PED 318. Similarly, the inner surface 314 of the lower region 312 may be configured to reflect EO radiation, such that EO radiation emitted by the emitters 301A passes through the PED support 308 reflects off of the inner surface 314 and irradiates a lower portion of the PED 318. As such, interior 309 of the apparatus 300 may be configured such that EO radiation emitted by the emitter 301A irradiates the entire surface of the PED 318, and EO radiation emitted by the emitter 301B irradiates the entire surface of the PED 318. Therefore, in some embodiments, the emitters 301A and 301B may be configured to emit EO radiation of different types and/or at different wavelengths to target different types of contaminants.

The apparatus 300 may further comprise a charging module 303 configured to charge the PED 318 while the PED 318 is within the interior 309 of the apparatus 300. Accordingly, the apparatus 300 may be configured to simultaneously sanitize and charge the PED 318. The apparatus 300 may further comprise a controller (not depicted in FIG. 3) configured to control the operation of the emitters 301A and 301B and the charging module 303. The controller may be coupled to a status indicator module 305 configured to display status information pertaining to the apparatus 300. The status indicator module 305 may comprise a light-emitting diode (LED) or other display mechanism, which may display colors indicative of the operational mode of the apparatus 300. For example, the status indicator module 305 may emit a red color while the apparatus 300 is sanitizing the PED 318 and may display a green color after a sanitization cycle is complete (e.g., after the PED 318 has been exposed to EO radiation for a particular time period). The status indicator module 305 may be further configured to display a charge state of the PED 318 (e.g., display a first color while the PED 318 is charging and a second color after the PED 318 is fully charged).

In FIG. 3, the apparatus 300 is depicted in an open configuration in which the interior 309 of the apparatus 300 is accessible. The apparatus 300 may comprise a close configuration in which the interior 309 is inaccessible and/or sealed, as described above. The apparatus 300 may be closed by use of a hinge member 316 coupling the upper region 313 to the lower region 312. The apparatus 300 may further comprise a latch or other securing mechanism (e.g., magnet or the like) configured to maintain the apparatus 300 in a closed configuration. In some embodiments, the apparatus 300 may comprise a gasket 317 that is configured to prevent EO radiation from leaking from the interior 309 of the apparatus 300. The gasket 317 may comprise an extruded portion and a grooved portion that are configured mate together to seal the interior 309 of the apparatus 300.

The apparatus 300 may further comprise an acoustic output, conduit, or exit 307 configured to provide an acoustic pathway between a speaker of the PED 318 and the exterior of the apparatus 300. As described herein, the acoustic exit 307 may be configured to prevent EO radiation from escaping the interior 309; the acoustic exit 307 may be configured to prevent EO leakage by use of a curved shape, absorptive surface, or the like.

Although not depicted in FIG. 3, the apparatus 300 may further comprise a controller, power module, detection module, sanitization module, and/or other modules as described herein.

Figure 4:
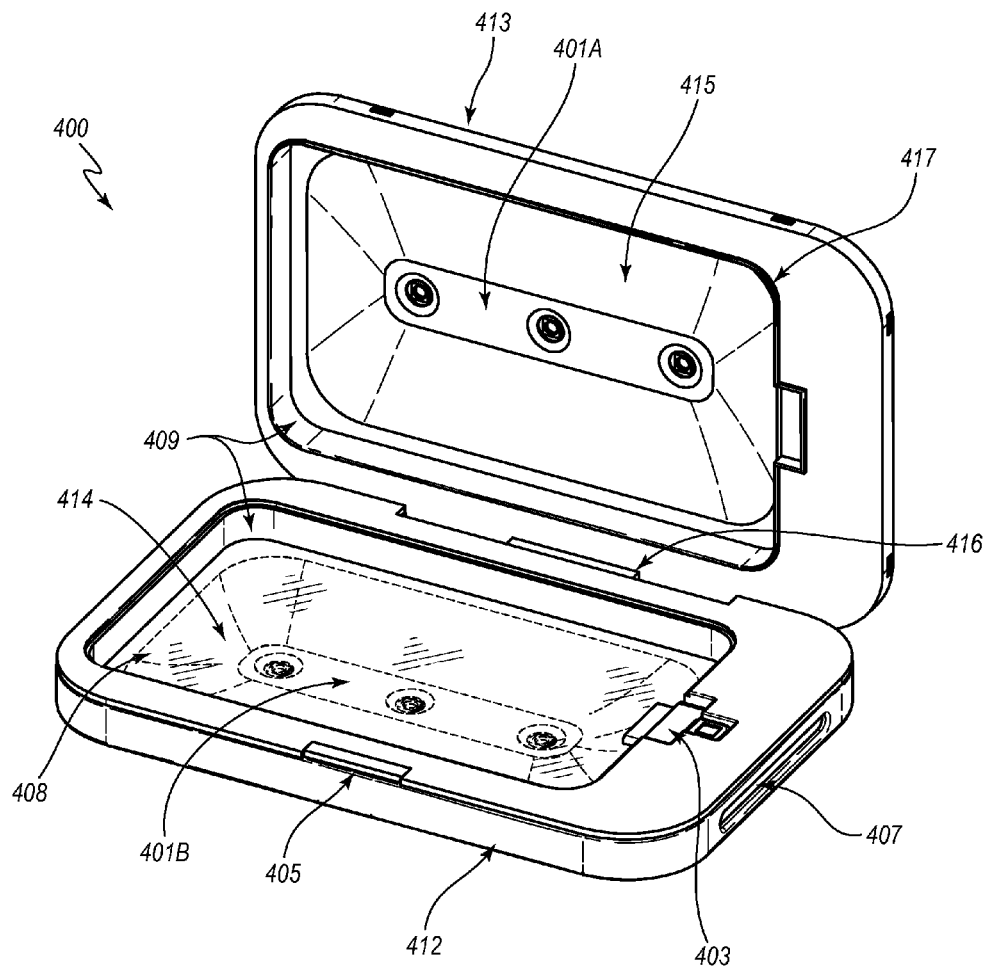
FIG. 4 depicts another embodiment of an apparatus for sanitizing a portable electronic device.

FIG. 4 depicts another embodiment of an apparatus for sanitizing a PED. In FIG. 4, the PED is omitted to better depict certain features of the embodiment. The apparatus 400 may comprise an interior compartment 409 comprised of an upper portion 413 having an upper inner surface 415 and a lower portion 412 having a lower inner surface 414. In some embodiments, the upper inner surface 415 and/or lower inner surface 414 may be configured to reflect and/or diffuse incident EO radiation.

The apparatus 400 may further comprise upper emitters 401A and lower emitters 401B. The apparatus 400 may further comprise a support plate 408 configured to hold a PED between the upper emitters 401B and the lower emitters 401A. The support plate 408 may be configured to be transparent to EO radiation emitted by the upper emitters 401B and/or lower emitters 401A. Accordingly, the apparatus 400 may be configured to irradiate an entire surface of a PED in the interior 409.

The apparatus 400 may further comprise a charge module 403 configured to charge a PED in the interior of the apparatus 400, and an acoustic opening 407 configured to provide for acoustic transmission from the interior 409 to the exterior of the apparatus 400. The apparatus 400 may be placed in a closed configuration by closing the upper portion 413 to the lower portion 412 by use of a hinge 416 connecting the portions 413 and 412. The interior 409 may be further sealed by use of rim and step structure 417, which may comprise a raised rim on the upper portion 413 and a corresponding step structure on the lower portion 412 configured to mate with rim.

Although not depicted in FIG. 4, the apparatus 400 may further comprise a controller, power module, detection module, sanitization module, and/or other modules as described herein.

Figure 5:
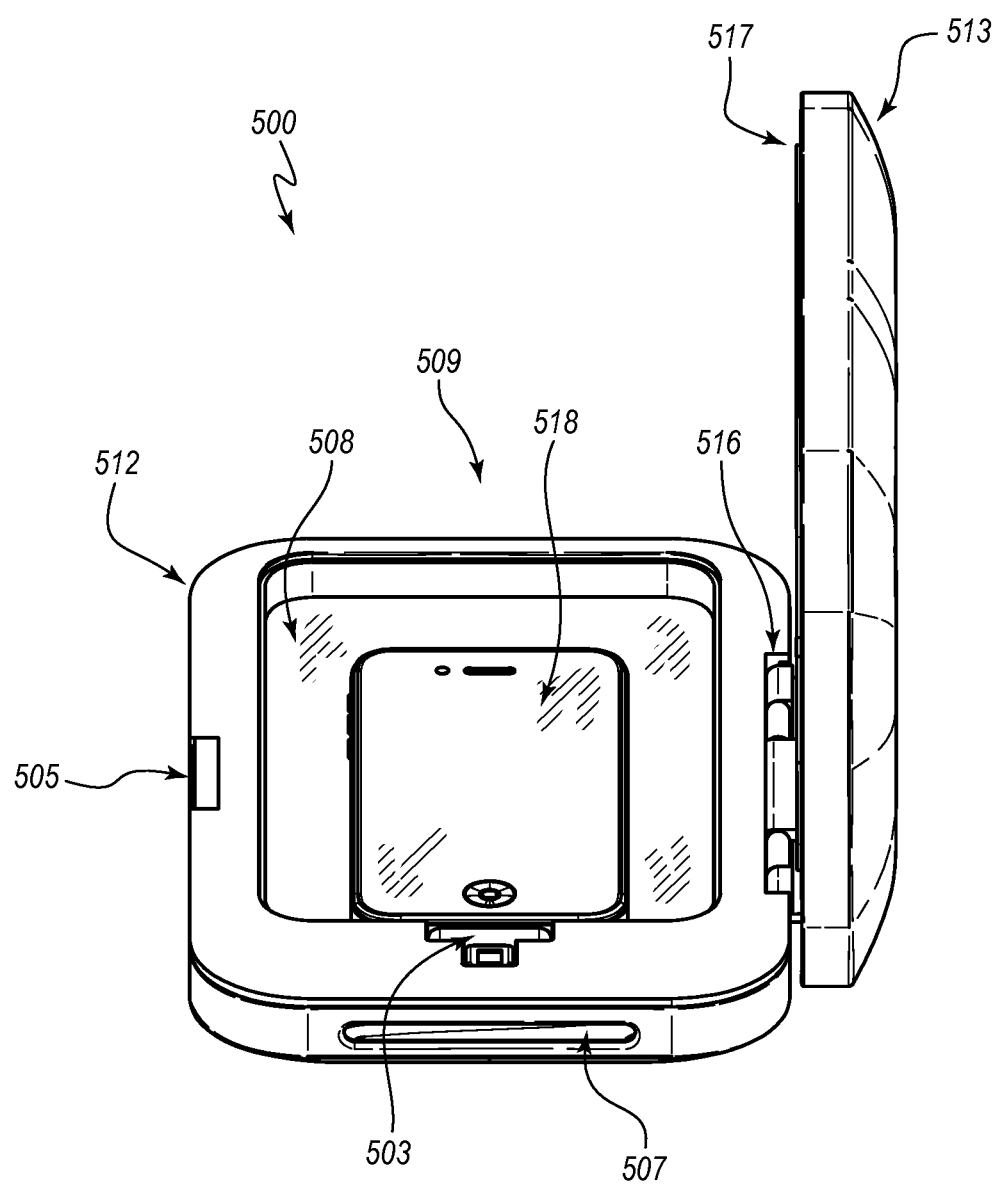
FIG. 5 depicts another embodiment of an apparatus for sanitizing a portable electronic device.

FIG. 5 depicts another embodiment of an apparatus 500 for sanitizing a PED 518. As described above, the apparatus 500 comprises an enclosure interior region 509 configured to receive the PED 518. The enclosure may comprise a clamshell configuration comprising an upper portion 513 and a lower portion 512 connected by a hinge 516. Although not depicted in FIG. 5, the apparatus may comprise one or more EO emitters configured to emit EO radiation into the interior of the enclosure 509. The EO emitter(s) may be disposed within the upper portion 513 and/or the lower portion 512. The PED 518 may be held between the upper and lower portions 513 and 512 by a transparent support 508. The transparent support 508 may be transparent to the EO radiation emitted by the emitters of the apparatus 500. The apparatus 500 may further comprise an acoustic exit 507 configured to acoustically couple the interior of the enclosure 509 to the exterior of the apparatus 500, while preventing EO radiation from being emitted from the enclosure 509.

The apparatus 500 may further comprise a charging module 503 configured to charge the PED while the PED is being sanitized within the enclosure 509. A status indicator module 505 may indicate an operational status and/or mode of the apparatus 500, as described above. Although not depicted in FIG. 5, the apparatus 500 may further comprise a power module configured to power the EO emitters and/or charging module 503 and a controller configured to control the operation of the EO emitters and/or charging module 503.

Although not depicted in FIG. 5, the apparatus 500 may further comprise a controller, power module, detection module, sanitization module, emitters, and/or other modules as described herein.

Figure 6:
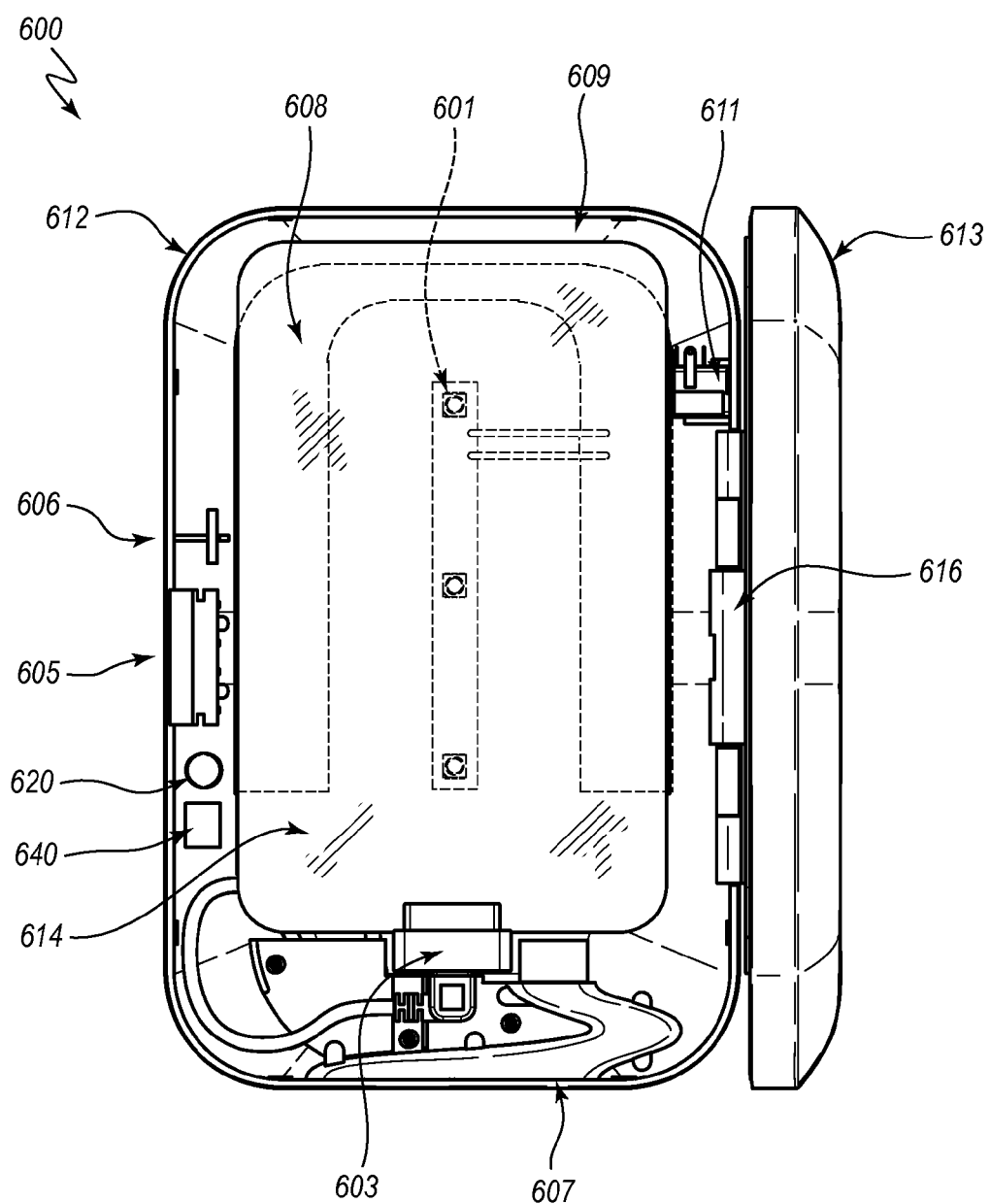
FIG. 6 depicts a cut-away view of another embodiment of an apparatus for sanitizing a portable electronic device.

FIG. 6 is a cut-away view of another embodiment of an apparatus 600 for sanitizing a PED. The apparatus 600 may comprise a lower region 612 and an upper region 613 coupled in a clamshell configuration by a hinge 616.

The apparatus 600 may comprise EO emitters 601 disposed on the lower region 612 of the apparatus 600. The emitters 601 may be configured to emit EO radiation into an interior region 609 of the apparatus 600, as described above. Although not depicted in FIG. 6, the apparatus 600 may further comprise one or more EO emitters disposed on the upper region 613 of the apparatus 600. The inner surface 614 of the lower region 612 and/or the inner surface of the upper region 613 may be configured to reflect and/or diffuse EO radiation within the interior region 609 of the apparatus 600. The support member 608 may be transparent to EO radiation. Accordingly, the apparatus 600 may be configured to expose an entire surface of a PED placed within apparatus 600 to EO radiation.

The apparatus 600 may further comprise a controller 640 configured to control the operation of the emitters 601, charging module 603, status indicator module 605, and/or other modules and/or components of the apparatus 600.

The apparatus 600 may comprise a power module 611 configured to receive input power from an external power source (e.g., power socket, battery, DC power source, or the like) and/or convert the input power into a form suitable for use by one or more components and/or modules of the apparatus 600. For example, the power module 611 may be configured to convert an alternating current (AC) power signal into a direct current (DC) power signal for use by the charging module 603. The power input module 611 may be further configured to power the emitters 601, status indicator module 605, controller 640, and/or other modules of the apparatus 600.

In some embodiments, the apparatus 600 may comprise a detection module 606 configured to determine whether the apparatus 600 is in a closed configuration. The detection module 606 may comprise a magnetic switch configured to detect when the lower region 612 is in contact with (and/or in close proximity to) the upper region 613. In response to determining that the apparatus 600 is in a closed configuration, the controller 640 may enable the emitters 601 (e.g., allow the emitters 601 to emit EO radiation into the interior region 609 of the apparatus 600).

In some embodiments, apparatus 600 may further comprise a securing mechanism 620 configured to secure and/or maintain the apparatus 600 in a closed configuration. In the FIG. 6 embodiment, the securing mechanism 620 may comprise a magnet configured to secure the lower region 612 to the upper region 613. The securing mechanism 620 may be further configured to determine whether the apparatus 600 is in a closed configuration, as described above.

The apparatus 600 may further comprise an acoustic conduit 607 configured to acoustically couple the interior region 609 to the exterior of the apparatus. The acoustic conduit 607 may be further configured to prevent EO radiation from escaping the interior region 609 and/or leaking from the apparatus 600. As shown in FIG. 6, the acoustic conduit 607 may comprise a curved shape, such that there is no optical path (e.g., line of sight path) through the acoustic conduit 607. In addition, the acoustic conduit 607 (and/or surface thereof) may be formed from a material that is configured to absorb the EO radiation. Accordingly, acoustic outputs of a PED within the interior region may reach the exterior of the apparatus 600, and EO radiation may be blocked from escaping the apparatus. In some embodiments, the acoustic conduit 607 may be further configured to amplify acoustic outputs of the PED.

Figure 7:
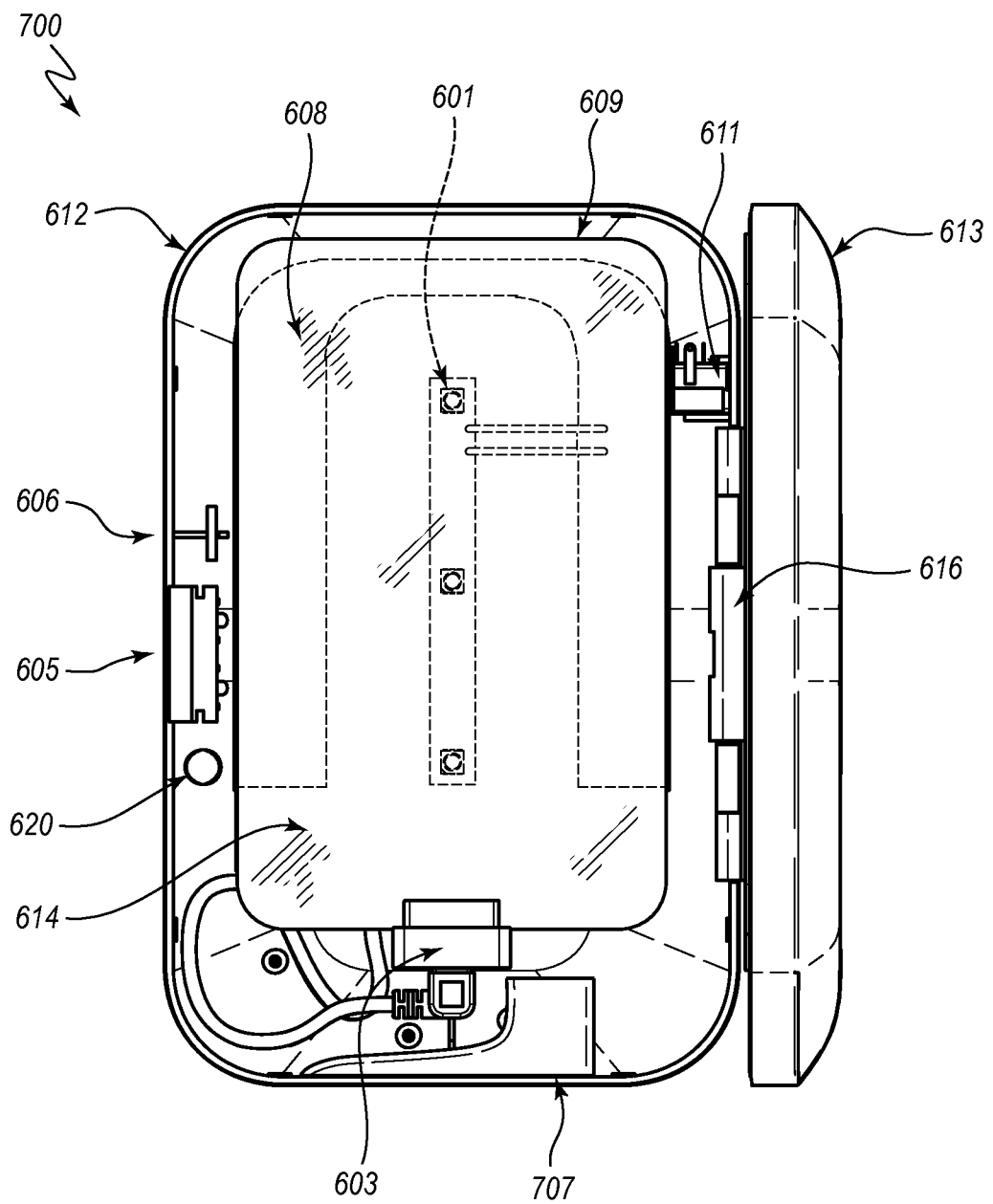
FIG. 7 depicts a cut-away view of another embodiment of an apparatus for sanitizing a portable electronic device.

FIG. 7 depicts another embodiment of an apparatus 700 for sanitizing a PED. As shown in FIG. 7, the acoustic conduit 707 may comprise an opening within the lower portion 612 of the apparatus 700. The acoustic conduit 707 may comprise an amplifying horn structure and/or shape configured to provide for the efficient transfer of sound from the interior 609 to the exterior of the apparatus 609. As described above, the acoustic conduit 707 may be further configured to prevent EO radiation leakage by use of absorptive materials, one or more baffles, a shape of the acoustic conduit 707, or the like.

Figure 8:
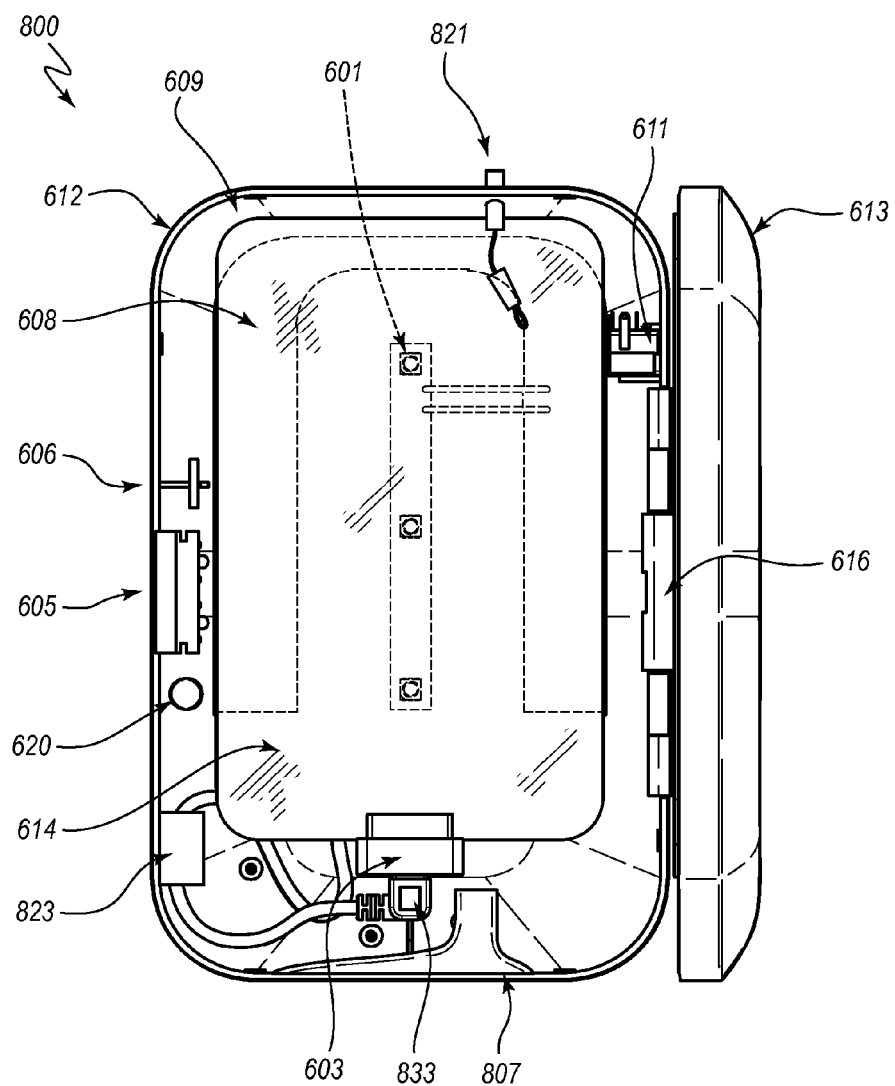
FIG. 8 depicts a cut-away view of another embodiment of an apparatus for sanitizing a portable electronic device.

FIG. 8 depicts another embodiment of an apparatus 800 for sanitizing a PED. The acoustic conduit 807 of the apparatus 800 may be configured to provide an acoustic pathway or channel between the interior 609 the lower region 612. In alternative embodiments, the acoustic conduit 807 may be disposed within the upper region 613, or other portion of the apparatus 800.

The apparatus 800 may further comprise an electronic connector 821 configured to connect an output of the PED within the interior 609 of the apparatus 800 to an external receiver (not shown). The electronic connector 821 may comprise any suitable connection means including, but not limited to: a 2.5 mm audio jack, a 3.5 mm audio cable, a Universal Serial Bus (USB) connector, or the like. The electronic connector 821 may comprise a male end disposed with the interior of the apparatus 800, which may be configured to interface with an electronic output of a PED, and a corresponding female connection configured to interface with the external receiver. For example, the electronic connector 821 may comprise a male 3.5 mm audio cable configured to interface with the audio output (e.g., headphone jack) of the PED coupled to a 3.5 mm audio jack accessible to the external receiver. The electronic connector 821 may be sealed and/or otherwise configured to prevent EO radiation from leaking from the apparatus 800. In some embodiments, the external connector 821 may be included in lieu of the acoustic conduit 807 (e.g., the acoustic conduit 807 may be removed and/or blocked). Alternatively, and as depicted in FIG. 8, the apparatus 800 may comprise both the electronic connector 821 and the acoustic conduit 807.

The apparatus 800 may comprise other types of electronic connectors, for example, the charging module 603 may be configured to charge the PED and provide a data and/or audio connection to the PED. Accordingly, in some embodiments, the apparatus 800 may be configured to act as a dock for the PED. For example, the charging module 603 may be coupled to a docking connector 823 configured to couple the PED to an external computing device, such as a personal computer, docking station, or the like. The docking connector 823 may comprise a USB connector, IEEE 1394 connector (Firewire), proprietary connector, or the like.

In some embodiments, the charging module 603 may comprise a universal charging connector 833 configured to interface to one or more different types of PEDs. For example, the universal charging connector 833 may comprise a USB connector, configured to interface with one or more proprietary connectors.

As disclosed above, the various embodiments of apparatuses for sanitizing a PED may comprise an open configuration in which the interior compartment and/or enclosure for the PED are accessible, and a closed configuration in which the interior of the apparatus is closed and/or sealed. FIG. 9 depicts embodiments of an apparatus 900 for sanitizing a PED in a closed configuration. The apparatus 900 may comprise a clamshell configuration as depicted in FIGS. 2-8. Accordingly, the apparatus 900 may comprise an upper region or portion 913 and a lower region or portion 912 connected by a hinge 916 (or other configurable connection mechanism). As depicted in FIGS. 9A-D, when in the closed configuration the interior portion or region of the apparatus is not accessible (e.g., is sealed). In the closed configuration, the apparatus 900 may prevent EO radiation from leaking therefrom. Therefore, and as described above, the upper region or portion 913 and/or the lower region or portion 912 may comprise a gasket or other sealing mechanism (e.g., dovetail structure) configured to block optical pathways from the interior portion of the apparatus 900 to the exterior of the apparatus 900.

As shown in FIG. 9D, an acoustic conduit 907 may be provided in the lower region or portion 912 of the apparatus 900. The configuration and/or shape of the acoustic conduit 907 may block optical paths between the interior of the apparatus 900 and the exterior of the apparatus 900. Alternatively, or in addition, the acoustic conduit 907 may be comprised of materials configured to absorb and/or block EO radiation. The lower region or portion of the apparatus 900 may further comprise a power module 911, which may be configured to receive a power connection from an external power source, such as a wall socket, power converter (AC/DC converter), or the like. Although not depicted in FIGS. 9A-D, the apparatus 900 may further comprise a sanitizing module (including one or more emitters), a PED support configured to hold a PED between the upper and lower portions or regions 912 and 913 of the apparatus 900, a detection module configured to detect closure of the apparatus 900, a controller, and so on, as described herein.

The apparatus 900 may further comprise an HMI module 930, which may be configured to receive user input pertaining to the operation of the apparatus 900. The HMI module 930 may comprise one or more buttons, switches, displays, actuators, or other input mechanisms. The HMI module 930 may provide for controlling sanitization functions of the apparatus 900 (e.g., activating the EO emitters of the apparatus 900), controlling charging functions of the apparatus 900, and so on. The HMI module 930 may further comprise a timer input through which a user may specify and/or select a sanitization time for the apparatus, select the EO radiation types, wavelengths, and/or intensity for use in sanitizing the PED, and so on. The HMI module 930 may be further configured to display the operational status and/or mode of the apparatus, such as sanitization status, sanitization time, charging status, charging time, and so on. The HMI module 930 may comprise a status indicator module 905, which may be configured to display status information. As depicted in FIGS. 9A and 9B, the status indicator module 905 may be implemented from the input components of the HMI module 930. Alternatively, the status indicator module 905 may be implemented together with the input components in a single interface module, such as an interactive touch screen, LCD display, or the like.

Figure 10:
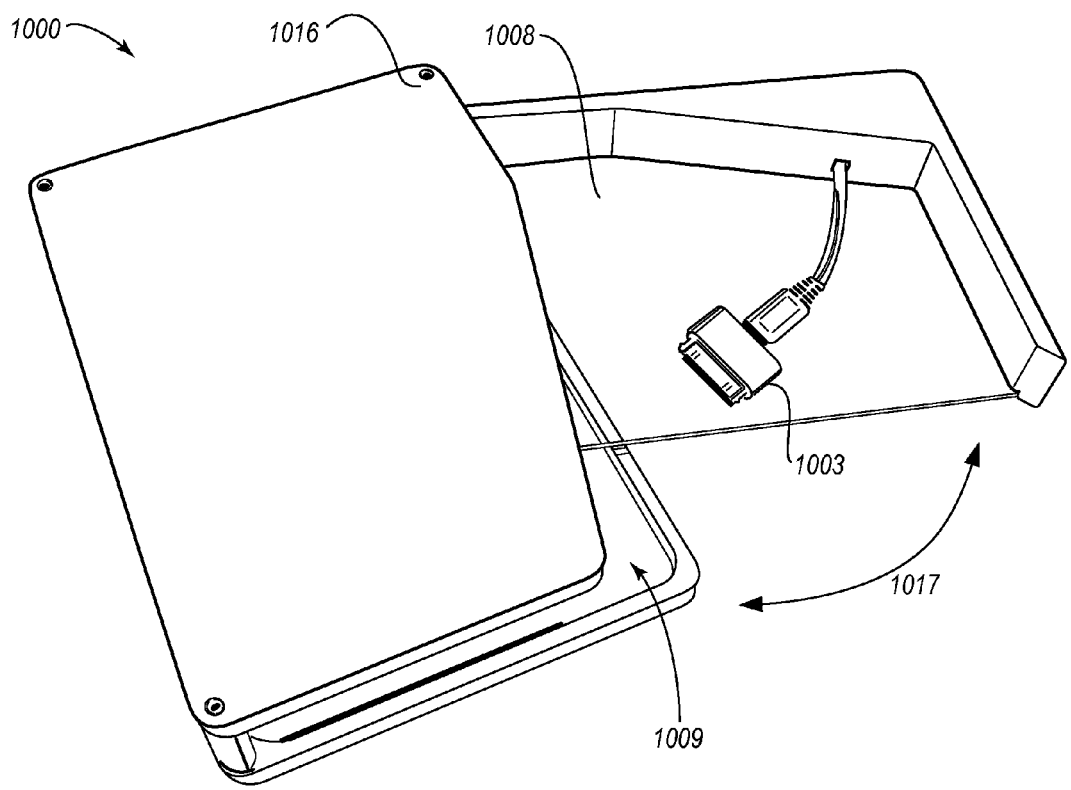
FIG. 10 depicts another embodiment of an apparatus for sanitizing a portable electronic device.

FIG. 10 depicts another embodiment of an apparatus 1000 for sanitizing a PED. The apparatus 1000 may comprise a sliding PED support member 1008 configured to receive a PED. In the open configuration of the apparatus 1000, and as depicted in FIG. 10, the PED support member 1008 may rotate 1017 outside of the interior portion or region 1009 of the apparatus 1000 by use of rotatable connector 1016 (e.g., hinge, or the like). In the closed configuration of the apparatus 1000, the PED support member 1008 may rotate 1017 into the interior region 1009. In the closed configuration, the interior portion 1009 may be opaque to EO radiation (e.g., sealed with respect to EO radiation) such that EO radiation emitted within the interior region or portion 1009 of the apparatus 1000 does not escape therefrom. The apparatus 1000 may further comprise a charging module 1003 configured to charge the PED, as described above.

Although not depicted in FIG. 10, the apparatus 1000 may further comprise a sanitizing module (including one or more emitters), a detection module configured to detect closure of the apparatus 1000 (e.g., a magnet switch or other detector on the PED support 1008), a controller, an acoustic conduit, a power module, an HMI module, and so on, as described above.

As disclosed above, the PED sanitization apparatuses disclosed herein may comprise a controller configured to control the operation of the sanitization module. The controller may be configured to irradiate the PED for a particular amount of time with one or more different types and/or wavelengths of EO radiation, and so on. The controller may be further configured to prevent the sanitization module from operating unless the apparatus is in a closed configuration (e.g., sealed with respect to EO radiation). The controller may comprise and/or be communicatively coupled to a machine-readable storage medium, such as a memory, firmware, or the like. The storage medium may comprise instructions configured to cause the controller to implement a method for controlling operation of a PED sanitization device.

Figure 11:
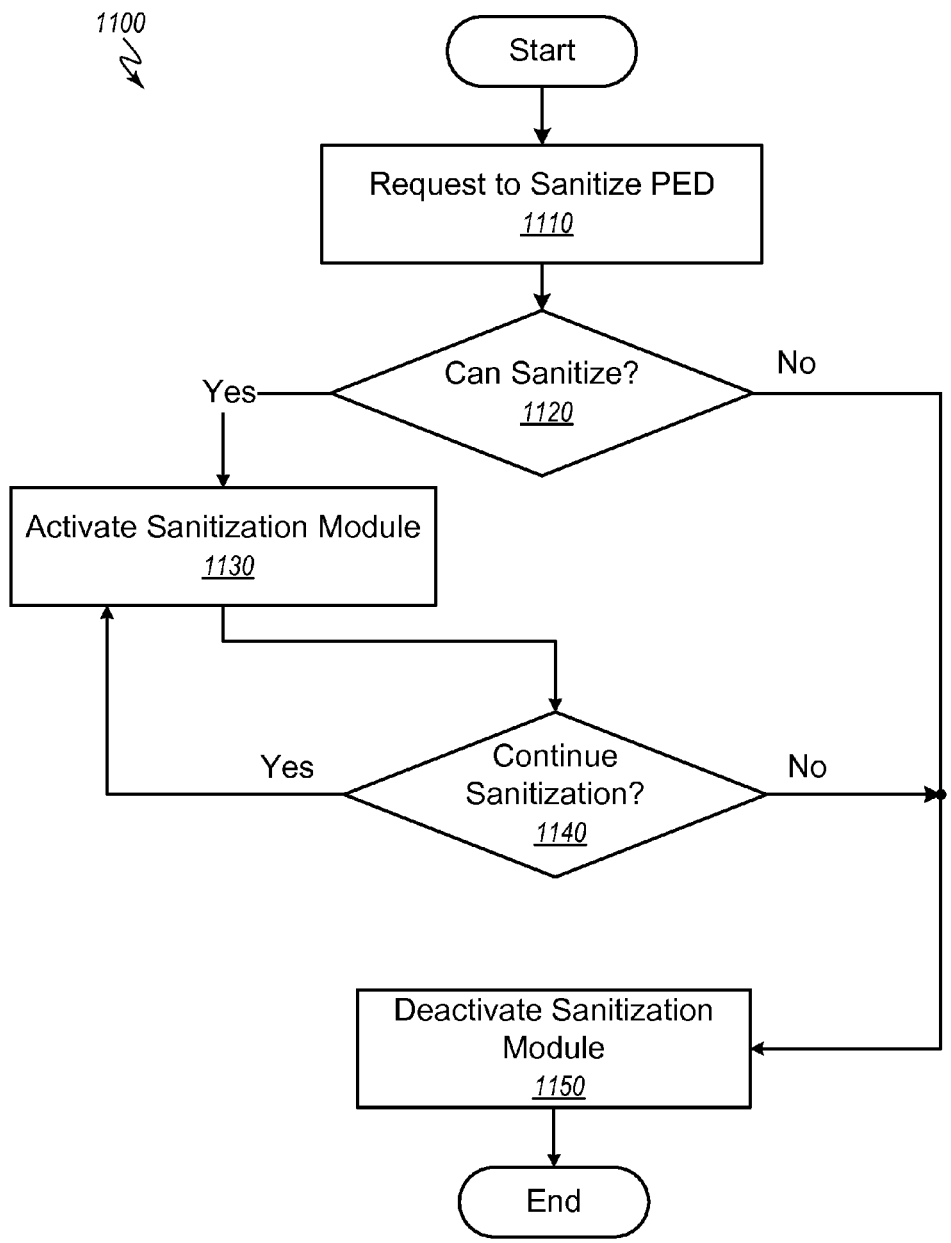
FIG. 11 is a flow chart of one embodiment of a method for sanitizing a portable electronic device.

FIG. 11 is a flow diagram of one embodiment of a method for controlling the operation of a PED sanitization device. The steps of FIG. 11 may be implemented by a controller (e.g., controller 140 and/or 640 described above). The controller may be configured to implement the method 1100 by use of one or more instructions stored on a machine-readable storage medium. The storage medium may be non-transitory, such as a hard disk, solid-state memory, electrically erasable memory, or the like.

Step 1110 may comprise receiving a request to sanitize a PED. Step 1110 may comprise detecting closure of a PED sanitization apparatus, detecting insertion of a PED into the apparatus, a user request (by use of a HMI 150 and/or input module 154), actuation of an input, a power-on condition, or the like.

Step 1120 may comprise determining whether the controller can perform the requested sanitization function. Step 1120 may comprise determining whether the sanitization apparatus is in a closed configuration, as described above. Accordingly, step 1120 may comprise evaluating the status of one or more detection mechanisms, such as switches, latches, or the like, by use of, inter alia, a detection module 164. Step 1120 may comprise determining that each of the detection mechanisms indicates that the apparatus is closed. If so, the flow may continue to step 1130; otherwise, the flow may continue to step 1150.

Step 1130 may comprise activating the sanitization module 110 to sanitize the PED. Step 1130 may comprise activating and/or configuring one or more EO emitters to irradiate an interior region, portion, and/or enclosure comprising the PED. Step 1130 may comprise configuring the EO emitters to emit EO radiation of particular types, wavelengths, and/or intensity according to a sanitization pattern or program, as described above. Step 1130 may comprise activating the sanitization module 110 in accordance with one or more user settings or preferences set via the HMI module 150 and/or one or more automatic settings and/or configurations, as described above.

Step 1140 may comprise monitoring operation of the apparatus to determine whether sanitization should continue. The sanitization operation activated at step 1130 may comprise sanitizing the PED for a particular amount of time and/or in accordance with a particular pattern or program. Step 1140 may, therefore, comprise determining whether the sanitization operations are complete. Step 1140 may further comprise monitoring the closure configuration of the apparatus. The step 1140 may comprise interrupting sanitization (e.g., deactivating the sanitization module 110 at step 1150) in response to determining that the apparatus is no longer in the closed configuration.

In some embodiments, step 1140 may further comprise displaying an indication of an operational status or mode of the apparatus via one or more HMI modules or components, such as the status indicator module 152 described above.

Step 1150 may comprise deactivating the sanitization module 110. Step 1150 may further comprise indicating a reason for the deactivation via, inter alia, the HMI module 150 and/or status indicator module 152. For example, the HMI module 150 may indicate that the deactivation of step 1150 occurred due to completion of a sanitization cycle, process, and/or pattern, interruption due the apparatus not being in a closed configuration, or the like. The method 1100 may end until a next request to sanitize a PED is detected at step 1110.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of one or more of the terms "about," "approximately," "substantially," and "generally." For each such reference, it is to be understood that, in some embodiments, the value, feature, or characteristic may be specified without approximation. For example, where such a qualifier is used, the terms includes within its scope the qualified word in the absence of the qualifier.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment. Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any embodiment require every feature shown in a particular drawing.

Unless otherwise noted, the terms "a" or "an" are to be construed as meaning "at least one of." In addition, for ease of use, the words "including" and "having" are interchangeable with and have the same meaning as the word "comprising." Recitation of the term "first" with respect to a feature or element does not necessarily imply the existence of a second or additional such feature or element.

We claim:

1. An enclosure configured to sanitize a portable electronic device, comprising:
    a case comprising an interior portion configured to hold a portable electronic device and comprising an upper portion and a lower portion,
    two or more emitters comprising an upper emitter configured to emit electro-optical radiation into the interior portion from the upper portion and a lower emitter configured to emit electro-optical radiation into the interior portion from the lower region;
    a transparent support configured to maintain the portable electronic device between the upper emitter and the lower emitter, wherein the support is configured such that an entire surface of the portable electronic device is exposed to electro-optical radiation emitted by one or more of the emitters;
    a charging module configured to charge the portable electronic device;
    a power module configured to power the charging module and the two or more emitters such that the two or more emitters emit electro-optical radiation while the charging module charges the portable electronic device; and
    an acoustic conduit configured to provide an acoustic pathway between the interior portion and an exterior of the case and to block an optical pathway between the interior portion and the exterior of the case, wherein the acoustic conduit comprises an electro-optical absorptive material positioned in the acoustic conduit, and wherein the electro-optical absorptive material is configured to absorb the electro-optical radiation emitted by the two or more emitters to prevent electro-optical radiation leakage through the acoustic conduit.

2. The apparatus of claim 1, further comprising:
  a hinge unit to couple the upper portion to the lower portion and to selectively configure the case in an open configuration in which the interior portion is accessible and a closed configuration in which the interior portion is sealed;
  a detection module configured to determine whether the case is in the closed configuration; and
  a controller configured to prevent the two or more emitters from emitting electro-optical radiation when the case is not in the closed configuration.

3. An apparatus for sanitizing a portable electronic device, comprising:
  an enclosure comprising an interior compartment comprising an upper interior surface and a lower interior surface, the interior compartment configured to receive a portable electronic device;
  an emitter configured to emit electro-optical radiation into the interior compartment;
  a support member configured to maintain the portable electronic device between the upper interior surface and the lower interior surface, wherein the support member is transparent to electro-optical radiation emitted by the emitter such that an entire surface of the portable electronic device is exposed to the emitted electro-optical radiation; and
  an acoustic conduit configured to provide an acoustic pathway between the interior compartment and an exterior of the apparatus and to block an optical pathway between the interior portion and the exterior of the enclosure, wherein the acoustic conduit comprises an electro-optical absorptive material positioned in the acoustic conduit, and wherein the electro-optical absorptive material is configured to absorb the electro-optical radiation emitted by the emitter to prevent electro-optical radiation leakage through the acoustic conduit.

4. The apparatus of claim 3, wherein the emitter comprises an upper emitter configured to emit electro-optical radiation from an upper region of the interior compartment and a lower emitter configured to emit electro-optical radiation from a lower region of the interior compartment.

5. The apparatus of claim 3, wherein one or more of the upper interior surface and the lower interior surface are configured to reflect electro-optical radiation emitted by the emitter, such that the entire surface of the portable electronic device is exposed to the emitted electro-optical radiation.

6. The apparatus of claim 3, wherein the enclosure comprises an open configuration and a closed configuration, wherein in the open configuration, the interior compartment of the enclosure is accessible, and wherein in the closed configuration, the interior compartment of the enclosure is closed, and wherein, in the closed configuration, the enclosure is configured to prevent electro-optical radiation emitted into the interior compartment by the emitter from escaping the enclosure.

7. The apparatus of claim 6, further comprising a detection module configured to determine whether the enclosure is in the open configuration, the emitter is configured to deactivate in response to the detection module determining that the enclosure is in the open configuration.

8. The apparatus of claim 7, wherein the detection module comprises one or more of a switch, a contact sensor, a magnetic sensor, a capacitive sensor, and a resistive sensor.

9. The apparatus of claim 3, further comprising:
  a charging module configured to charge the portable electronic device within the interior compartment; and
  a power module configured to power the charging module and the two or more emitters.

10. The apparatus of claim 3, wherein the acoustic conduit comprises a plurality of baffles to prevent electro-optical radiation leakage while allowing acoustic signals to pass.

11. The apparatus of claim 3, wherein the electro-optical absorptive material comprises a membrane of electro-optical absorptive material to block electro-optical radiation and pass acoustic signals.

12. The apparatus of claim 3, wherein a shape of the acoustic conduit is configured to block an optical path between the interior compartment and the exterior of the enclosure.

13. The apparatus of claim 12, wherein the shape of the acoustic opening comprises a curvature configured to block the optical path between the interior compartment and the exterior of the enclosure.

14. The apparatus of claim 3, wherein the electro-optical absorptive material comprises filaments of electro-optical absorptive material to absorb sanitizing electro-optical radiation while allowing acoustic signals to pass.

15. The apparatus of claim 3, wherein the acoustic opening is configured to amplify an acoustic output of the portable electronic device.

16. An apparatus for sanitizing a portable electronic device, comprising:
  a compartment configured to receive a portable electronic device;
  an emitter configured to emit electro-optical radiation into an interior of the compartment; and
  an acoustic opening in the compartment configured to provide for transmission of an acoustic signal generated by the portable electronic device within the compartment to an exterior of the compartment, and to prevent transmission of electro-optical radiation emitted into the interior of the compartment to the exterior of the compartment, wherein the acoustic opening comprises an electro-optical absorptive material positioned in the acoustic opening, and wherein the electro-optical absorptive material is configured to absorb the electro-optical radiation emitted by the two or more emitters to prevent electro-optical radiation leakage through the acoustic opening.

17. The apparatus of claim 16, wherein the compartment comprises an upper surface and a lower surface, and wherein one or more of the upper surface and the lower surface are configured to reflect electro-optical radiation emitted by the emitter, the apparatus further comprising a support member configured to maintain the portable electronic device between the upper surface and the lower surface, wherein the support member is transparent to the electro-optical radiation emitted by the emitter such that a surface of the portable electronic device is exposed to electro-optical radiation emitted by the emitter.

18. The apparatus of claim 16, further comprising:
  a detection module configured to determine whether the compartment is in a closed configuration in which the interior of the compartment is sealed to electro-optical radiation; and
  a controller configured to prevent the emitter from emitting electro-optical radiation when the compartment is not in the closed configuration.

19. The apparatus of claim 18, wherein the controller is configured to cause the emitter to emit electro-optical radiation for a time period set by user configuration.

20. The apparatus of claim 16, further comprising:
  a charging module configured to charge the portable electronic device within the compartment; and a power module configured to power the charging module and the emitter.

\* \* \* \* \*